United States Patent [19]

Tigliev

[11] Patent Number: 5,288,043
[45] Date of Patent: Feb. 22, 1994

[54] BALANCED SUSPENSION SYSTEM FOR SURGICAL MICROSCOPE

[76] Inventor: George S. Tigliev, House 55, Apt. 190, Code 191104, St. Petersburg, Prospect Blyukhera,

[21] Appl. No.: 944,092
[22] Filed: Sep. 11, 1992
[51] Int. Cl.⁵ .............................................. F16L 3/00
[52] U.S. Cl. .................................. 248/123.1; 248/278; 248/585; 359/384
[58] Field of Search ...................... 248/122, 123.1, 124, 248/280.1, 585, 660, 182, 228, 279; 359/384

[56] References Cited

U.S. PATENT DOCUMENTS

| | | | |
|---|---|---|---|
| 2,967,458 | 1/1961 | Stone, Jr. | 248/123.1 X |
| 3,776,614 | 12/1973 | Kloots et al. | 359/384 X |
| 4,332,426 | 6/1982 | Speicher | 248/661 X |
| 4,548,373 | 10/1985 | Komura | 248/122 |
| 4,881,709 | 11/1989 | Nakamura | 359/384 X |
| 5,074,651 | 12/1991 | Naeamine | 359/384 |

Primary Examiner—Ramon O. Ramirez

[57] ABSTRACT

A balanced suspension system for a surgical investigative instrument, such as a surgical microscope, is configured so that the amount of force to move the microscope in any direction is approximately equal, and when the suspension system is unlocked to move the microscope no residual forces will spontaneously move the microscope. The suspension system comprises a generally vertical support structure, a levered assembly extending out therefrom, a gimbal mount assembly connected adjacent one end of the levered assembly. The gimbal mount assembly includes a bracket arm having a first joint member at one end thereof and an instrument bracket, for holding the microscope, connected to a second end thereof by a second joint member. The instrument bracket includes a third joint member, so that the center of mass of the microscope lies within the three planes of motion permitted by the first, second and third joint members.

8 Claims, 2 Drawing Sheets

BALANCED SUSPENSION SYSTEM FOR SURGICAL MICROSCOPE

BACKGROUND OF THE INVENTION

1. Field of the Invention

The present invention relates to a suspension system for use with a surgical microscope and, more particularly, to such a suspension system that maintains the surgical microscope in a balanced state for ease of motion.

2. Setting of the Invention

In the field of medical technology there exists a need for a mobile surgical microscope suspension system that permits the rapid and nearly effortless movement of the microscope when desired, as well as the firm fixation of the microscope when desired. Ideally, such a suspension system would have minimal mass and dimensions, a maximal number of positions for the microscope, uniformity of applied force for movement in all directions, reliable fixation in desired positions, and absence of spontaneous motion in an unlocked state.

Existing surgical microscope suspension systems are of relatively large size to provide desired mass and rigidity. However, this mass results in an increased moment of inertia so movement is difficult to precisely control. Usually, these surgical microscope suspension systems include costly and complex arrangements of counterbalances and springs. These systems have a problem of differences in the amount of force that need be applied to move the microscope in different directions, and a problem of spontaneous spring-induced movement when the system is unlocked.

Examples of prior types of suspension systems are disclosed in U.S. Pat. Nos. 3,762,797 and 3,891,301. These systems include a massive base and relatively large counterweight system used to provide stability to the microscope when in the unlocked position. In order to move the microscope in various directions, various amounts of force are required and a significant inertial force interferes with the precise positioning of the microscope.

The Olympus OME 5000 includes a massive base and a plurality of levers to maintain the microscope in a given position when the system is in the unlocked state. Again, various amounts of force are required to move the microscope in various directions.

Another type of microscope suspension system is disclosed in Soviet Union Scientific Research Institute of Governmental Patent Expertise, No. 0142 (1990), "Microscope For Neurosurgery" developed by the inventor hereof. This system still has the disadvantage of the differences of the amount of force needed to move the microscope in various directions. Other suspension systems are disclosed in the following U.S. Pat. Nos.: 3,973,748; 4,523,732; 4,741,607; 4,815,832; 4,881,709 and 4,953,822.

SUMMARY OF THE INVENTION

The present invention has been contemplated to overcome the foregoing deficiencies and meet the above described needs. Specifically, the present invention comprises a balanced suspension system for a surgical investigative instrument, such as for a surgical microscope. The suspension system comprises a generally vertical support structure with a levered assembly extending out therefrom, and a gimbal mount assembly selectively rigidly connected adjacent one end of the levered assembly. The gimbal mount assembly comprising a bracket arm having a first joint member at one end thereof and an instrument bracket connected to a second end of the bracket arm by a second joint member. The instrument bracket including a third joint member.

The surgical microscope is mounted to the instrument bracket so that the center of mass of the microscope lies within the three planes of motion permitted by the first, second and third joint members. This configuration allows a "balanced" state of the microscope, i.e. there are no counteracting, spring induced forces that will cause the microscope to drift once the suspension system has been unlocked, without the need for complex balancing devices (levers, springs, counterweights, etc.). Further, the suspension system provides ease of movement, due to its relatively lower mass and size, with equal amount of force needed for movement to various positions.

DETAILED DESCRIPTION OF THE PREFERRED EMBODIMENTS

The present invention is a balanced suspension system for a surgical investigative instrument, which for the purposes of this discussion will be assumed to be a surgical microscope. However, it should be understood that any other type of instrument could be used with the present invention, such as eye examination instruments, dental instruments and patient examination instruments. The suspension system of one preferred embodiment of the present invention comprises a generally vertical support structure having a levered assembly, such as a pantograph, extending out therefrom, and a gimbal mount assembly connected adjacent one end of the levered assembly.

The gimbal mount assembly comprises a bracket arm having a first joint member at one end thereof and an instrument bracket connected to a second end thereof by a second joint member. The instrument bracket is adapted to receive and hold the surgical microscope and permit rotation thereof by way of a third joint member.

The gimbal mount assembly is configured so that center of mass of the surgical microscope held by the instrument bracket lies with the three planes of motion permitted by the three joint members, i.e. roll, pitch and yaw. By this arrangement the surgical microscope is "balanced", i.e. the forces acting on the microscope are canceled out so that, when the suspension assembly is unlocked to permit movement of the microscope, no residual forces spontaneously move the microscope.

Figure 1:
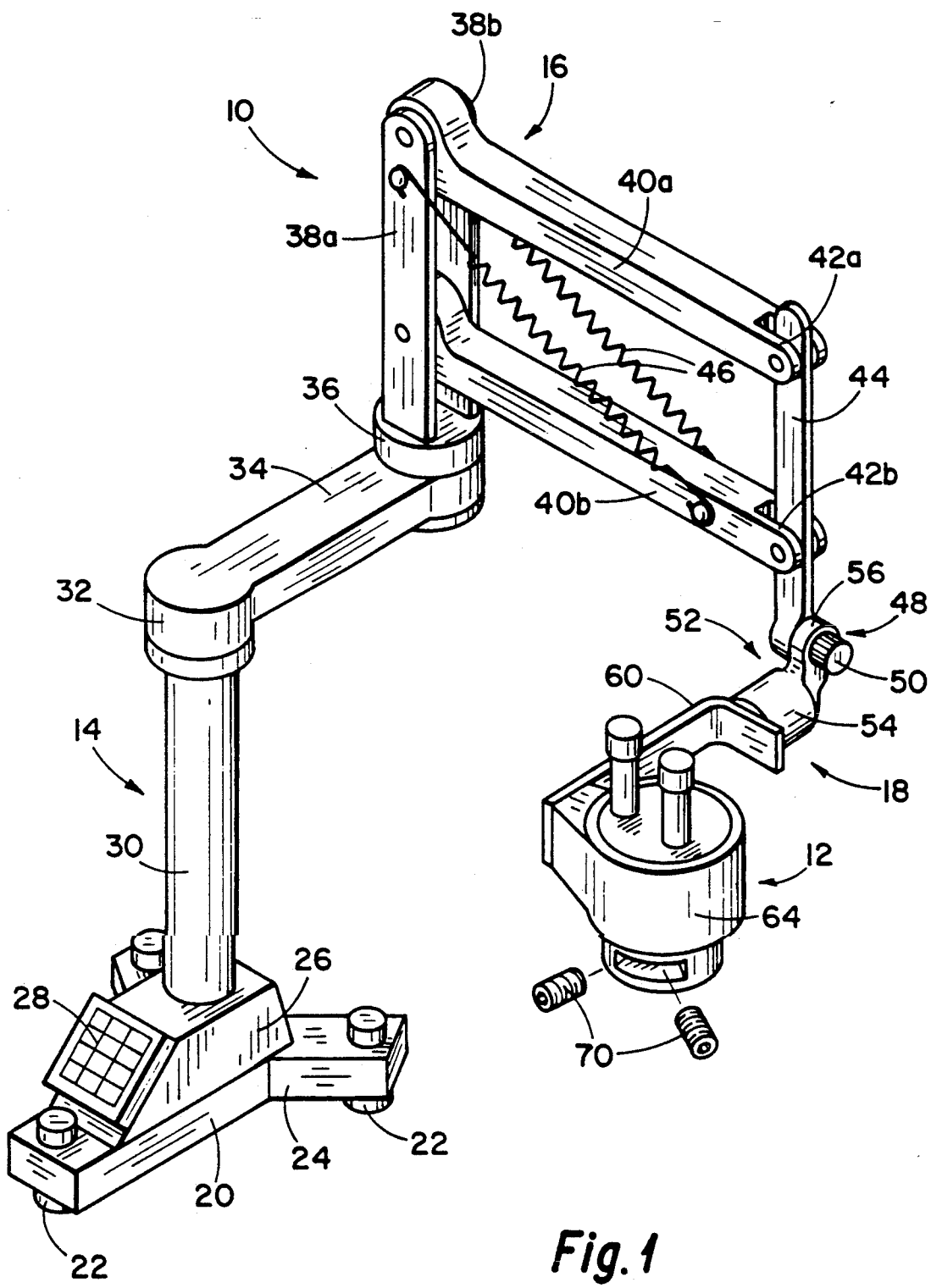
FIG. 1 is an upright, perspective view of a suspension system for a surgical investigative instrument in accordance with one preferred embodiment of the present invention.

One preferred embodiment of the present invention is shown in FIG. 1 wherein a balanced suspension system 10 for a surgical investigative instrument, such as a surgical microscope 12, includes a generally vertical support structure 14, a levered assembly 16 extending from the support structure 14, and a gimbal mount assembly 18 extending from the levered assembly 16. The surgical microscope 12 is removably mounted within the gimbal assembly 18 in a manner described below.

The support structure 14 can be of any desired configuration that can provide stability and the desired range of movement. One preferred configuration includes a base 20, having adjustable elastomeric pads, wheels or rollers 22 on an underside thereof (if desired), and being of sufficient weight and floor contacting surface area to provide the desired stability, such as by including outwardly extending legs 24. An electrical power supply 26 (interconnected to a source of 110 v. or 220 v. electrical power) and control panel 28 are mounted to the base 20 and are in turn operatively electrically connected to the microscope 12 for providing electrical power to the lighting and imaging equipment (not shown) associated with the microscope 12. Further, the power supply 26 provides electrical power to motion limitation mechanisms, described below.

Extending generally vertically from the base 20 is at least one support column 30 with a swivel joint member 32 attached to an upper end thereof, which permits radial rotation of a suspension arm 34 (connected at one end thereto) in a horizontal plane about a vertical axis. At an opposite end of the suspension arm 34 is a swivel joint member 36, preferably of the same configuration as the joint member 32.

The levered assembly 16, in the form of a pantograph, is connected to the suspension arm 34 at the joint member 36, so that the levered assembly 16 can independently be moved radially in a horizontal plane about a vertical axis. The levered assembly 16 includes a support upright, and preferably for stability purposes, parallel support uprights 38a and 38b. Movably connected at one end to and lying between the support uprights 38a and 38b are spaced and parallel pantograph arms 40a and 40b, each of which includes a yoke 42a and 42b respectively at an opposite end thereof. Movably connected to the yokes 42a and 42b is a secondary support upright 44, which is configured to move vertically and in a parallel manner with respect to the support upright 38. One or more springs 46 extend from an upper portion of the support uprights 38a and 38b to an outer portion of the pantograph arm 42b, to provide a spring biasing to resist downward forces caused by the weight of the gimbal mount assembly 18 and microscope 12 connected to the secondary support arm 44, as described below.

Figure 2:
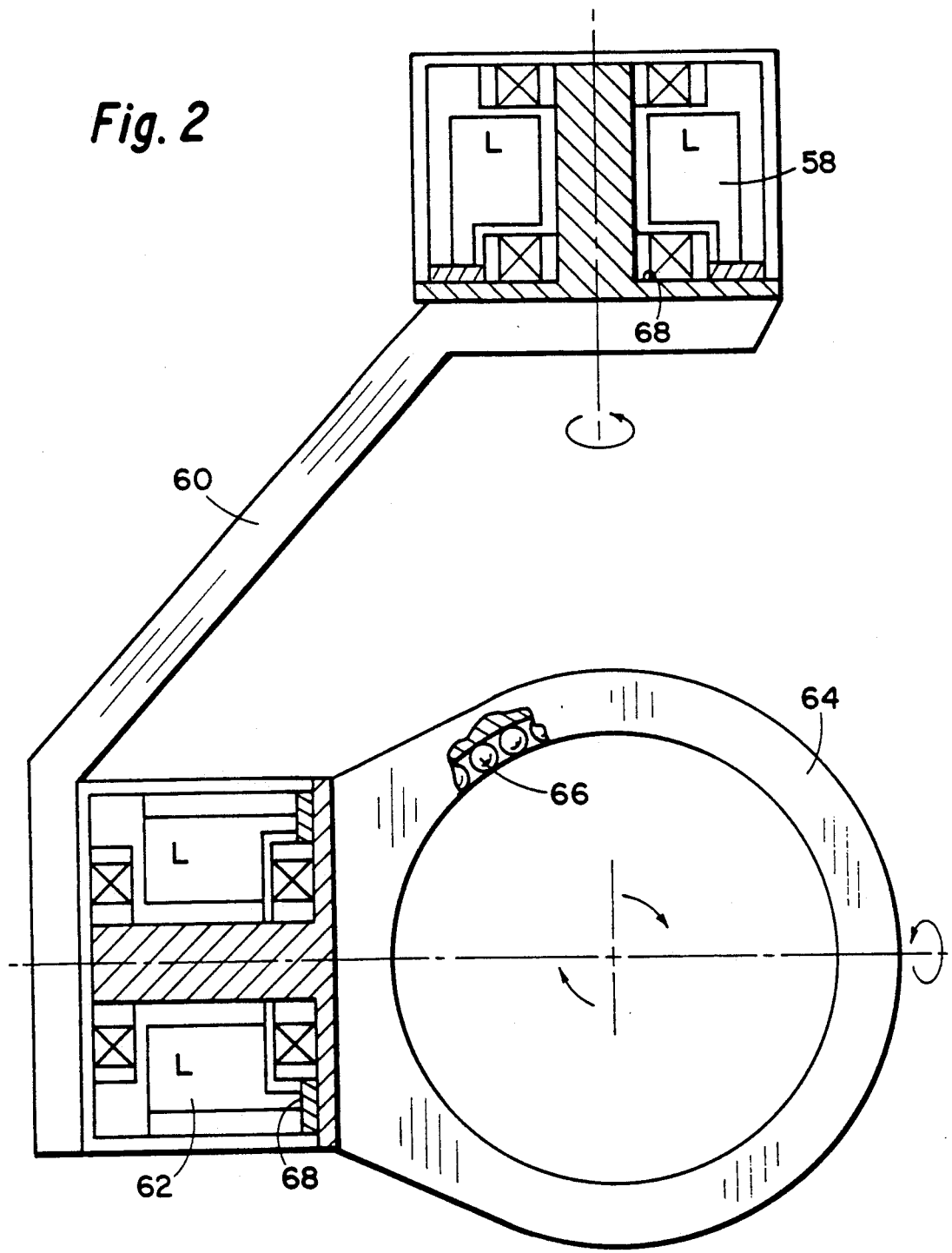
FIG. 2 is a horizontal sectioned view of a gimbal mount assembly for use in the suspension system of the present invention.

The lower end of the support arm 44 includes a friction lock connection 48 and knurled adjustment knob 50 onto which is movably mounted the gimbal mount assembly 18. A transverse bracket 52 includes a body 54 and an outwardly extending flange 56, which is received against and held in position by the friction lock connection 48. The interior of the body 54 includes a first joint member 58 (shown in FIG. 2) that provides movement to the gimbal mount assembly 18, and thus to the microscope 12, through a vertical plane about a horizontal axis. This motion can be considered as the "roll" component of movement for the microscope 12.

Extending generally horizontally out from the body 54 is a bracket arm 60 with a second joint member 62 (shown in FIG. 2) connected at an outer end thereof. The second joint member 62 provides movement to the gimbal mount assembly 18, and thus to the microscope 12, through a vertical plane about a horizontal axis perpendicular to the first joint member 58. This motion can be considered as the "pitch" component of movement for the microscope 12.

An instrument bracket 64 is connected to the second joint member 62, and is generally a cylindrical housing into which the microscope 12 is received and held. The interior of the cylindrical housing includes an annular third joint member 66 (shown in FIG. 2), in the form of a circumferential race that permits the microscope to rotate in a horizontal plane about a central vertical axis. This motion can be considered as the "yaw" component of movement for the microscope 12.

The configuration of the gimbal mount assembly 18 is specifically chosen to cooperate with the particular type, weight and size of instrument to be mounted into the instrument bracket 64 to provide for the balanced feature. Specifically, this balance feature is provided by ensuring that the center of mass of the microscope 12 lies within the three planes of motion (roll, pitch and yaw) permitted by the first, second and third joint members 58, 62 and 66. As has been described above, by configuring the suspension system 10 in this manner, the microscope 12 can be moved about in all planes with equal amounts of force and no residual forces will cause spontaneous movement of the microscope 12 when it is unlocked for movement.

To ensure that there are equal amounts of force needed to move the microscope 12 (and the suspension system 10 holding same), it is preferred that the joint members 32, 36, 58, 62 and 66 be of the same configuration. Such joint members can include sleeve bearings, roller bearings or ball bearings. Most preferably, the joint members include precision ball bearings for low mass and ease of movement.

To lock the suspension system, ie to prevent movement while the surgeon is looking through the microscope 12, friction locks or other suitable motion limitation mechanisms can be used within or adjacent the joint members 32, 36, 58, 62 and 66. Preferably, these mechanisms are electromagnetic locks comprising plates 68 that are freed from one another by the application of electrical power from the power supply 26, as is well known to those skilled in the art.

For positioning of the microscope 12, the surgeon depresses a foot switch (not shown), a button on one or more positioning handles 70 or a mouth switch (not shown) to energize the plates 68 so that the joint members are free to move to permit the desired placement of the microscope 12. When the switch has been released, the electrical power is shut off to cause the electromagnetic locks to ridgedly hold all of the joint members in a stable and secure position.

As described above, the suspension system of the present invention provides simplified construction over previous systems because a gimbal mount is used with the center of mass of the microscope lying within the three planes of motion to allow a "balanced" state when the suspension system is in an "unlocked" condition for movement of the microscope 12. This system does not need the use of special and complex levers, springs and counterweights, as did previous systems. Further, the suspension system of the present invention has an increased convenience of use as a result of the relative lightness and uniformity of amount of force needed for movement in any desired direction.

Whereas the present invention has been described in particular relation to the drawings attached hereto, it should be understood that other and further modifications, apart from those shown or suggested herein, may be made within the scope and spirit of the present invention.

What is claimed is:

1. A balanced suspension system for a surgical investigative instrument, comprising:
 a generally vertical support structure,
 a levered assembly extending out from one end of the support structure, and
 a gimbal mount assembly connected adjacent one end of the levered assembly, the gimbal mount assembly comprising:
 a bracket arm having a first joint member at one end threof and an instrument brakcet connected to a second end thereof by way of a second joint member, the instrument bracket including a third joint member; and
 the first joint member provides motion about a horizontal roll plane, the second joint member provided motion about a horizontal pitch plane perpendicular to the first plane, and the third joint member provides motion about a vertical yaw plane;
 whereby the center of mass of the surgical investigative instrument lies within the three planes of motion permitted by the first, second and third joint members.

2. A suspension system of claim 1 wherein the support structure comprises a support column with a base connected to a lower end thereof, and a generally horizontal suspension arm connected to an upper end thereof by way of a joint member.

3. A suspension system of claim 1 wherein the levered assembly comprises a pantograph.

4. A suspension system of claim 3 wherein the pantograph comprises at least one generally vertical support upright connected to a joint member on an outer end of a generally horizontal suspension arm which is connected to a support column, spaced and parallel pantograph arms connected at one end to the at least one support upright and connected at an opposite end to a generally vertical secondary support upright, and at least one spring connected between the at least one support upright and one of the pantograph arms.

5. A suspension system of claim 1 wherein the joint members and the first, second and third joint members include ball bearings.

6. A suspension system of claim 1 wherein the first, second and third joint members include motion limitation mechanisms.

7. A suspension system of claim 6 wherein the motion limitation mechanisms comprise electromagnetic locks.

8. A suspension system of claim 6 and including means for activation of the motion limitation mechanisms adjacent the surgical investigative instrument.

* * * * *